(12) United States Patent
Stefanchik et al.

(10) Patent No.: US 7,815,566 B2
(45) Date of Patent: Oct. 19, 2010

(54) METHODS FOR STABILIZING AND POSITIONING AN ENDOSCOPE AND SURGICAL PROCEDURES

(75) Inventors: David Stefanchik, Morrow, OH (US); Ragae M Ghabrial, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1125 days.

(21) Appl. No.: 11/458,900

(22) Filed: Jul. 20, 2006

(65) Prior Publication Data

US 2008/0021277 A1 Jan. 24, 2008

(51) Int. Cl.
*A61B 1/01* (2006.01)
(52) U.S. Cl. .................. 600/146; 600/101; 600/114
(58) Field of Classification Search ............ 600/101, 600/114, 146; 128/898; 606/139
See application file for complete search history.

(56) References Cited

U.S. PATENT DOCUMENTS

| | | | | |
|---|---|---|---|---|
| 5,037,021 A * | 8/1991 | Mills et al. | ............... | 227/175.1 |
| 5,813,976 A * | 9/1998 | Filipi et al. | ................. | 600/102 |
| 6,142,931 A * | 11/2000 | Kaji | ............................ | 600/114 |
| 6,231,561 B1* | 5/2001 | Frazier et al. | ................ | 604/500 |
| 6,699,263 B2* | 3/2004 | Cope | ........................... | 606/232 |
| 7,150,750 B2* | 12/2006 | Damarati | ................. | 623/17.11 |
| 2003/0130669 A1* | 7/2003 | Damarati | ..................... | 606/151 |
| 2004/0122473 A1* | 6/2004 | Ewers et al. | ................. | 606/222 |
| 2005/0192615 A1* | 9/2005 | Torre et al. | ................... | 606/192 |
| 2009/0216081 A1* | 8/2009 | Suzuki et al. | ............... | 600/115 |
| 2009/0222025 A1* | 9/2009 | Catanese et al. | ............ | 606/139 |

* cited by examiner

*Primary Examiner*—John P Leubecker (57) ABSTRACT

Methods for stabilizing and positioning an endoscope using various braided devices and suture techniques. Related endoscopic surgical procedures are also disclosed. A surgical method comprises introducing an endoscope into a patient's natural orifice. The endoscope is guided in a patient's alimentary tract lumen, the alimentary tract lumen being defined by the alimentary tract wall. One or more sutures are anchored at the target site of the surgical procedure. The sutures are tensioned to position the endoscope while the sutures pass through a working channel of the endoscope.

9 Claims, 12 Drawing Sheets

METHODS FOR STABILIZING AND POSITIONING AN ENDOSCOPE AND SURGICAL PROCEDURES

BACKGROUND

The present invention relates in general to surgical devices and procedures, and more specifically to endoscopic procedures and accessories for use with an endoscope.

Surgical procedures are often to treat and cure a wide range of diseases, conditions, and injuries. One with ordinary skill in the art will readily recognize the many benefits of minimally invasive surgery, as compared to open incisional, including less pain, shorter recovery time, less scarring, and lower cost. Surgeons typically use endoscopes during minimally invasive surgical procedures to visualize tissue within the patient. Laparoscopic surgery is one type of minimally invasive surgical procedures in which a surgeon uses ports to access and visualize the tissue site of interest within the abdominal cavity. Often laparoscopic surgery involves filled the abdominal cavity with an insufflatory fluid, such as carbon dioxide or saline, to provide adequate space to perform the intended surgical procedures. The insufflated cavity is generally under pressure and is sometimes referred to as being in a state of pneumoperitoneum. Another type of minimally invasive surgery involves entering the patient via natural openings (e.g., mouth, anus, vagina, urethra, and the like) and conducting inspection or treatment within the organ, sometimes referred to as intraluminal procedures. Still another type of minimally invasive surgery involves entering the patient via natural openings of the body and piercing organ walls to access inside the adnominal cavity, sometimes referred to as transluminal surgery.

Numerous endoscopic and minimally invasive surgical instruments have been developed that allow the surgeon to perform complex surgical procedures, whether laparoscopic, intraluminal, transluminal or otherwise, but no one has previously made or used a device or procedure in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, like reference numerals identify the same elements.

DETAILED DESCRIPTION

Figure 1:
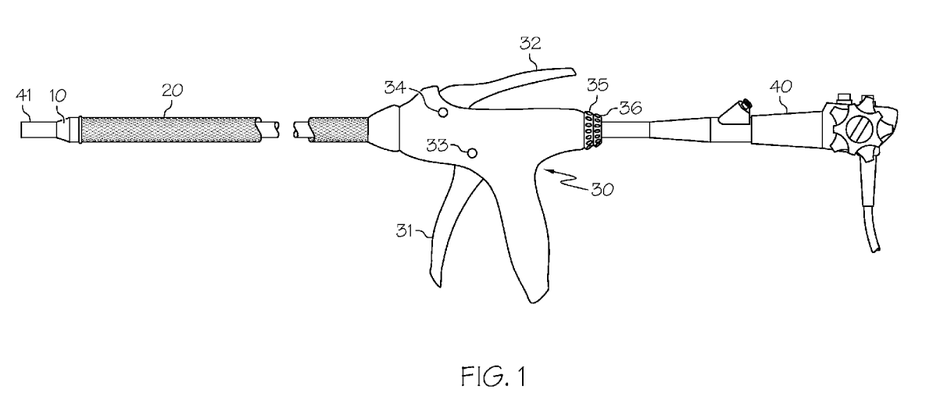
FIG. 1 depicts a braided endoscopic device.

FIG. 1 depicts a perspective view of a braided device with a standard endoscope (40) extending through a central lumen (5) of the braided device. The term "standard endoscope" hereinafter refers to a general utility endoscope, including but not limited to bronchoscopes, gastroscopes, enteroscopes, duodenoscopes, and colonoscopies. The outer diameter of a standard endoscope generally ranges from about 6 mm to about 14 mm. The braided device comprises a distal collar (10), a handle (30), and a flexible braided tube (20) having a length extending between the handle (10) and the distal collar (5). One feature of the braided device is that the flexible braided tube (20) is selectively lockable at a desired configuration, sometimes referred to as shape-lock. For instance, a surgeon may use the braided device to hold a distal portion (41) of the standard endoscope (40) in a desired orientation. In additional, a surgeon may use the braided device to steer a distal portion (41) of the standard endoscope (40) in a desired orientation. The standard endoscope (40) may be rotatably moveable around its central axis with respect to the braided device and the distal end of the standard endoscope (40) may be extended beyond the distal collar (10) of the braided device.

The braided flexible tube (20) may be formed by interweaving a plurality of filaments around a central mandrel via a braiding machine. The interwoven braid filaments may be capable of moving relative to each other. The term "filament" herein is broadly defined to cover any element with an elongated configuration, including but not limited to a thread, fiber, cord, string, yarn, twine, rope, line, cable, wire, ribbon, tape, or the like. The filaments in the braided flexible tube (20) may all be the same type and material, or a composite of different of types or materials. A maypole type of braiding machine, as sold by Steeger USA, Inc. of Spartanburg, S.C., or by the New England Butt Division of Wardwell Braiding Machine Company may be used in construction of the braided flexible tube (20). As one with ordinary skill in the art will recognize, braiding machines of this type use two groups of carriers, where each carrier carries a spool of the filament to be presented by the respective carrier. Carriers are arranged in a circular array around a braiding axis of the central mandrel and are driven in one direction about that axis. Carriers of the first group are arrayed around the braiding axis and are driven in clockwise direction for example. Carriers of the second group are also arrayed, in a circular array around the braiding axis, in an alternating order with respect to carriers of the first group, and are driven in the opposite direction about the braiding axis. As the carriers move, the filaments are pulled off their respective spools and laid out onto the central mandrel forming the braided flexible tube (20).

The filaments used to make the flexible braided flexible tube (20) could be made from, for example, polyester, cotton, polyamide, polyalkane, polyurethane, PET, PBT, nylon, PEEK, PE, glass fibre, metal wire, acrylic materials, and the like, or any composition of the mentioned materials. They may be in the form a monofilament or a multifilament and may have a cross section in the shape of any geometrical form, such as a cross section in the form of a rectangle, square or a circle. For instance, in case of a circle they may have a diameter range of about 0.005 to about 0.04 inches. People with ordinary skill in the art will appreciate that the porosity of the braided flexible tube (20) and the size of the windows (i.e., the spaces between the interlaced filaments) formed by the intersecting filaments are a function of the perpendicular distance (d) between the parallel filaments, the thickness of the filaments, and the intersection angle (A). The arrangement of the filament braiding will change the characteristics of the braided flexible tube (20). For example, the porosity of the braided flexible tube (20) influences its flexibility and its hoop strength. For instance, if all other variables are held constant, the lower the porosity of a braided tube then the higher its hoop strength becomes. Decreasing the initial intersection angle (A), increasing the thickness of the filaments or their numbers, and decreasing the perpendicular distance between the parallel filaments are all ways to reduce the porosity of the braided flexible tube (20). In one embodiment, the intersection angle (A) has an angle range of more than 0 degrees and less than 180 degrees. In another embodiment, the intersection angle range between 10 and 170 degrees.

Figure 2:
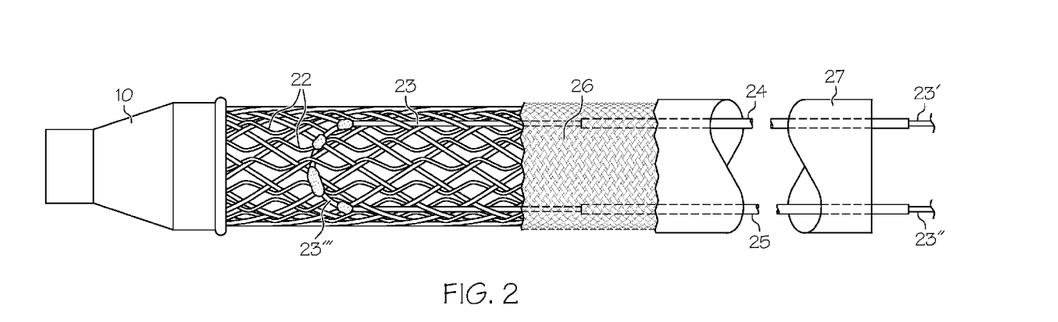
FIG. 2 depicts a distal portion of a braided device.

FIG. 2 depicts one example of a braided device with the outer layers being partially removed to show the internal components. In this embodiment the outer most layer is a flexible outer sleeve (27) that provides a barrier between the contents of a patient's body lumen and the internal components of the braided device. It may also have a relatively smooth surface to reduce the risk of injury to the lumen wall while the braided device is extended through the lumen. In one example the outer sleeve (27) is an elastomeric sheath. In another example, the outer sleeve (27) may be a braided sleeve that is coated with a polymer coating to provide a smooth outer surface. For instance, the braided flexible tube (20) may be dipped into a solution comprising the polymer. Polymers that may be used include but are not limited to polyvinyl chloride, polyolefin (e.g., polyethylene, polypropylene, ethylene-vinylacetate copolymer), polyamide, polyester (e.g., polyethylene terephthalate (PET), polybutylene terephthalate), polyurethane, polystyrene resin, fluoro-based resin (e.g., polytetrafluoroethylene, ethylene-tetrafluoroethylene copolymer), polyimide, and the like; and various elastomers such as polyurethane-based elastomer, polyester-based elastomer, polyolefin-based elastomer, polyamide-based elastomer, silicone rubber, latex rubber, and combinations thereof.

The braided device may also comprise a distal collar (10). In this embodiment the distal collar (10) in frustoconical with a distal end narrower than its proximal end; however, other geometries are also possible. The distal collar (10) is adapted to receive a distal portion of a standard endoscope (41) and provide a relatively tight fit such that the distal collar (10) can act as a frame of reference for that portion of the standard endoscope (40) allowing for stability and a better control over steering of the distal portion of the standard endoscope (41). The distal collar (10) can be made in a variety of different ways. In one embodiment, the distal collar (10) may be formed separately and then molded onto the distal end of the braided flexible tube (20). In yet another embodiment, a distal portion of the flexible braided tube (20) can be made into a distal collar (10) by configuring the braid at this portion to be in the shape of a cone and coating with a polymer coating.

FIG. 2 also shows an embodiment of the braided flexible tube (20) comprising longitudinal support members (22) that can be axially integrated into the wall of the braided flexible tube (20). The longitudinal support members (22) help prevent collapse of the braided flexible tube (20) upon its bending. Such collapse may hinder the movement of the standard endoscope (40) through the braided flexible tube (20). In one example, the longitudinal support members (22) may be interwoven in the braided flexible tube (20) and parallel to its central axis (22). Furthermore, they may be equally spaced apart from one another around a circumference of the braided flexible tube (20). A longitudinal support members (22) can be made from several materials such as for example polyester, cotton, polyamide, polyalkane, polyurethane, PET, PBT, nylon, PEEK, PE, glass fibre, metal wire or acrylic materials or any composition of the mentioned materials. It may have a cross section of any geometrical shape, such as a rectangle, square, circle, and the like. In case of a circle, it may have a diameter range of about 0.002 to about 0.040 inches. In another example, the longitudinal support members (22) could be formed from an elastic material. The longitudinal support members (22) may then be interwoven into wall of the braided flexible tube (20) while they are partially stretched. This configuration may expose the braided flexible tube to an initial axial compression reducing its porosity and providing better hoop strength. Once a bending force is applied on the braided flexible tube (20), the elastic longitudinal support members are stretched a little further which in turn translates into an opposite force that may pull the tube back to a first neutral position once the bending force is removed. Examples of elastic materials that may be used to form the longitudinal support members (26) include but not limited to silicon, urethane, pelithane, and the like.

FIG. 2 also shows a cable (23) disposed axially and being longitudinally translatable relative to the braided flexible tube (20), the cable (23) having a mounting portion (23''') attached to a region of the wall of the braided flexible tube (20) by interweaving and gluing along the circumference of the wall. The mounting portion of cable (23) may also be attached to the wall by a variety of different means including, for example, molding or clamping. Cable (23) may also comprise first (23') and second (23") longitudinal portions extending from the mounting portion (23''') of cable (23) alongside the braided flexible tube (20) towards its proximal end where they are connected to the handle (30). As shown here, the mounting portion (23''') is shared between the two longitudinal portions (23' & 23"), but each longitudinal portion could have its own discrete mounting portion. The first longitudinal portion (23') of the cable may extend into a first pipe (24) running alongside the braided flexible tube (20) proximal to the mounting portion of the cable. The second longitudinal portion (23") of the cable may extend into a second pipe (25) running alongside the braided flexible tube (20) proximal to the mounting portion of the cable. The first pipe (24) and the second pipe (25) can be made from a variety of different materials. In one example, they can be metal coil l-springs. In another example, they can be braided pipes comprised of a flexible polymer material such as for example polyester. The pipes may allow for movement of the longitudinal portions (23' & 23") of the cable (23) between the handle and the central portion of that cable. Actuation of the handle may apply tension on the longitudinal portions of the cable, which may be translated to the braided flexible tube (20) leading to bending towards the side of the tube where the cable is extended. Varying the degree of tension applied to the two longitudinal portions (23' & 23") of the cable can provide articulation of the braided flexible tube (20). The longitudinal portions (23' & 23") in this embodiment are circumferentially spaced between 0 and 180 degrees from one another. Naturally, more than two longitudinal portions may be positioned around the circumference of the braided flexible tube (20) in a variety of different circumferentially spaced configurations.

FIG. 2 also shows a flexible sheath (26) housing the braided flexible tube (20). The flexible sheath (26) may be a braided sheath with a relatively small porosity, and relatively high hoop strength. The flexible sheath (26) may resist circumferential expansion that may take place while the braided flexible tube (20) is under axial compression forces, which helps in maintaining the braided flexible tube (20) in a relatively rigid configuration. The flexible sheath (26) may also house pipes (24, 25). In one embodiment, the pipes may be interwoven into the wall of the flexible sheath (26). This configuration may prevent the pipes from bulging out when the distal portion of cable (23) are under tension. In yet another embodiment, the pipes may be attached to the surface of the flexible sheath (26) via, for example, glue.

Figure 3A:
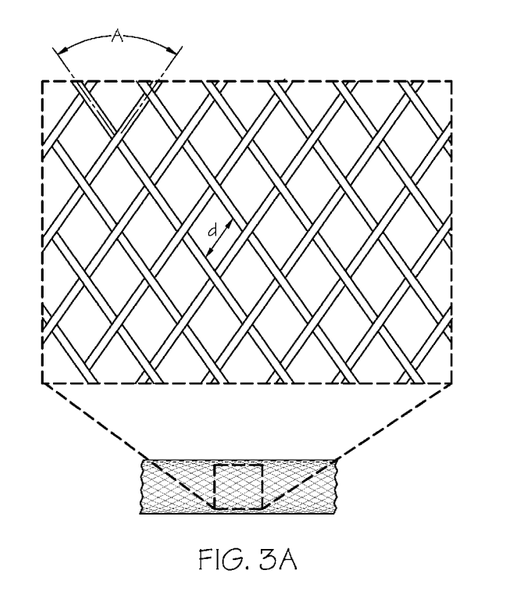
FIG. 3A depicts a section of the wall of a braided flexible tube.
Figure 3B:
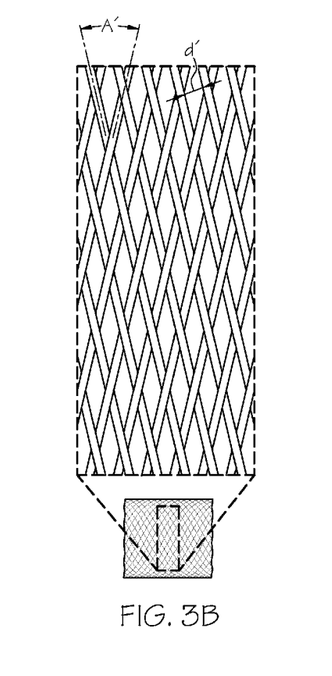
FIG. 3B depicts a section of the wall of a braided flexible tube.

FIGS. 3A&B depict the transition that may take place in the wall of the braided flexible tube (20) when exposed to axial compression upon actuation of the handle (30). Upon tensioning of the distal portions (23' & 23") of cable (23), the braid filaments of the flexible braided tube (20) will move relative to each other. The intersection angle (A) may drop to a smaller angle (A'), which in turn may decrease the perpendicular distance between the parallel braid filaments from a distance (d) to (d') reducing the porosity of the wall of the braided flexible tube (20) and decreasing its length from an initial length (L) to (L'). The reduction in porosity will yield an increase in the rigidity and hoop strength, which tends to locks it in a desired orientation.

Figure 4:
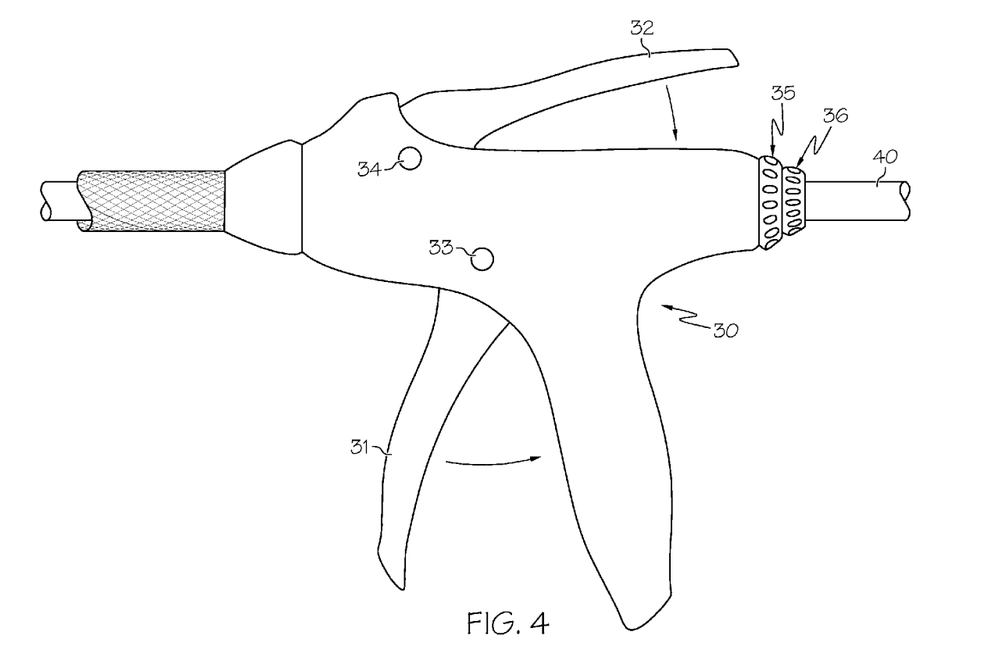
FIG. 4 depicts a handle of a braided endoscopic device.

FIG. 4 depicts one embodiment of the handle (30) of the braided device. Handle (30) may comprise a first actuation arm (31) which may be connected to a proximal end of a first cable and a second actuation arm (32) which may be connected to a proximal end of a second cable where the distal ends of the cables are attached to the wall of the braided flexible tube (20). The actuation arms (31 & 32) may be operatively associated with the braided flexible tube (20) such that actuating the first and second actuation arms may bend the braided flexible tube (20) in a certain orientation. Handle (30) may also comprise ratchets for selective locking of each actuation arm. An operator may actuate the first actuation arm (31) bending the braided flexible tube (20) to a first desired orientation and may then release the first actuation arm (31) allowing a first ratchet to lock the actuation arm in place. The operator may also actuate the second actuation arm (32) further bending the braided flexible tube (20) to a second desired orientation and may then release the second actuation arm (32) allowing a second ratchet to lock the actuation arm in place. Handle (30) may also comprise a first (33) and a second (34) lock release buttons, which upon pressing may release the locked ratchets. Fine-tuning of the positioning of the braided flexible tube (20) may be done via rotation knobs (35 & 36), which may selectively apply additional tension to a cable connected to an actuation arm once the actuation arm, is actuated and locked in place. For example, the first actuation arm (31) may be actuated and locked at a desired orientation applying tension to a proximal end of a cable that has a distal end connected to the wall of the braided flexible tube (20). An operator may then realize that further bending is required, at which point, the operator may twist knob (35) to apply additional differential tension to the cables resulting in orthogonal steering to the original steering position.

Figure 5A:
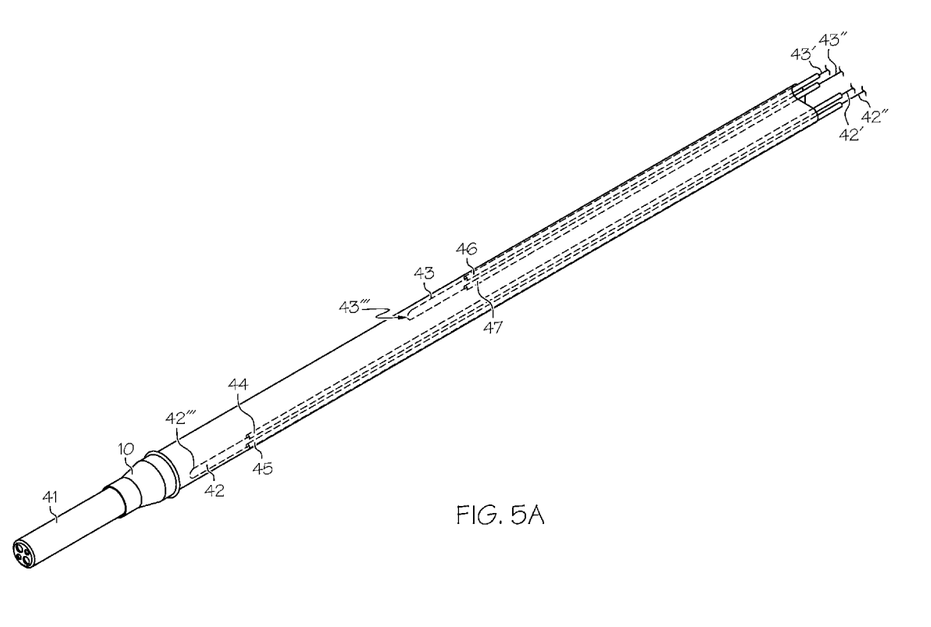
FIG. 5A depicts a braided endoscopic device in a neutral position.
Figure 5B:
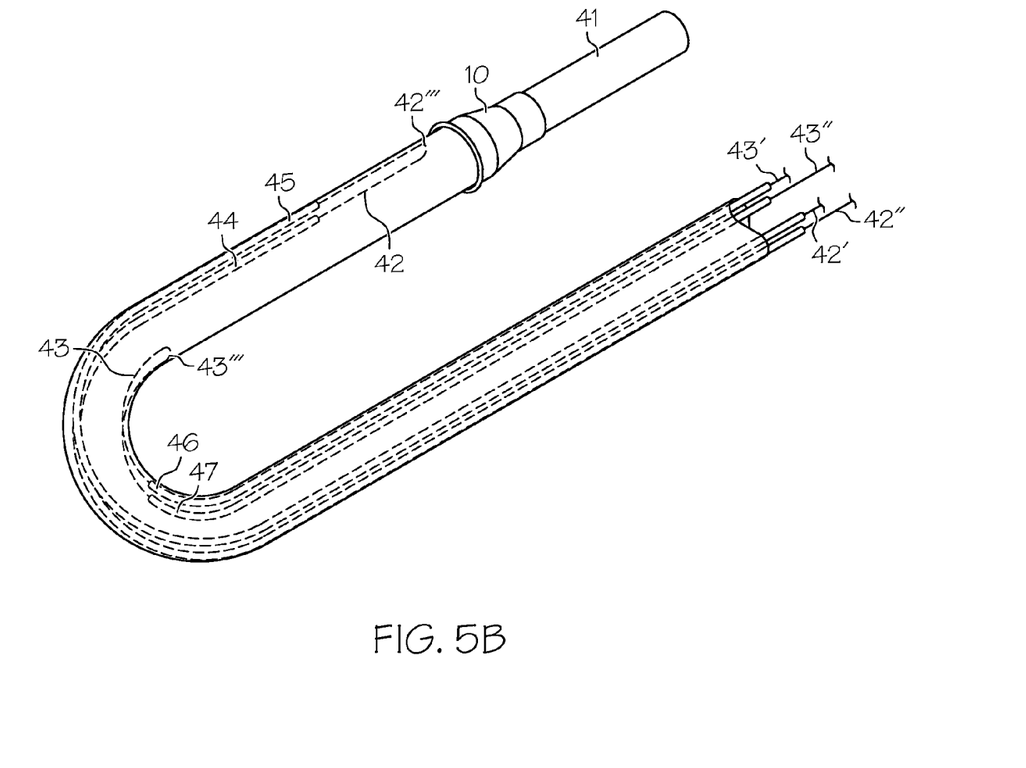
FIG. 5B depicts a braided endoscopic device in a bent position.
Figure 5C:
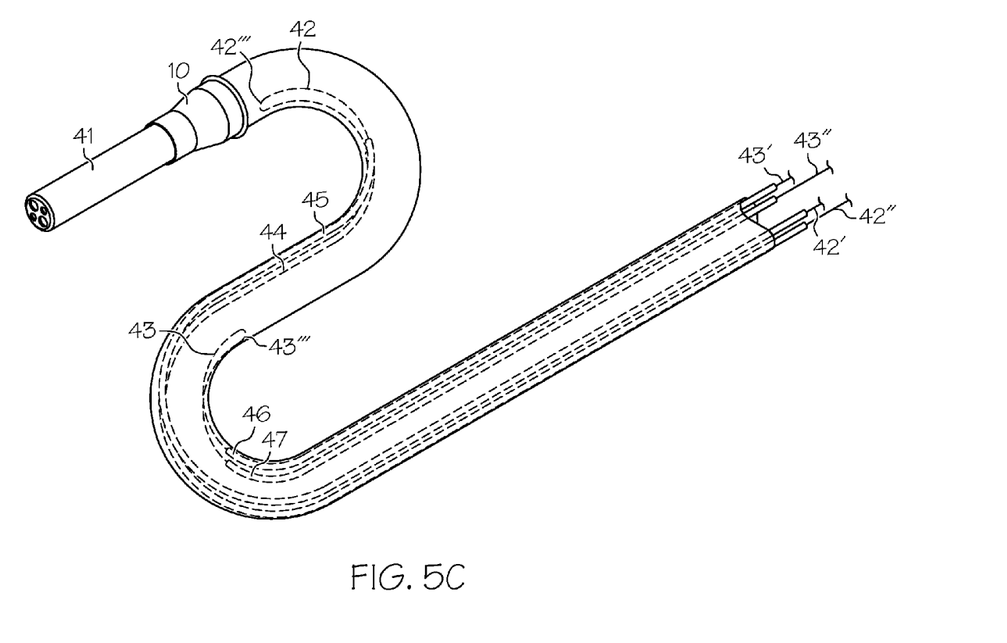
FIG. 5C depicts a braided endoscopic device in a compound bent position.

FIG. 5A depicts an embodiment of the braided device having the ability to bend at two separate regions along its length. In this embodiment, the braided device comprises a first (42) and a second (43) cables, each attached at a mounting portion along its length to a separate region along the wall of the braided flexible tube (20), where the mounting portion (42''') of the first cable (42) being at a distal location to that of the mounting portion (43''') of the second cable (43). The first (42) and second (43) cables may be disposed on opposite sides of the braided flexible tube or any desired angle. In this embodiment, they are disposed at a 60° angle. The longitudinal portions (42' & 42") of the first cable (42) are extended separately through pipes (44 & 45). The longitudinal portions (43' & 43") of the second cable (43) are extended separately through pipes (46 & 47). FIG. 5B shows the longitudinal portions (43' & 43") of the second cable (43) being retracted which leads to bending of the braided device at a first location. FIG. 5C shows the longitudinal portions (42' & 42") of the first cable (42) being retracted which leads to bending the braided device at a second location distal to the first location. In addition, three or more cables may be utilized depending on the degree of articulation needed. The braided flexible tube (20) may be selectively locked at a portion along its length by preventing the braid filaments at such portion of the braided flexible tube (20) from moving relative to each other. In one embodiment, the braid filaments may be prevented from moving relative to each other by coating of such portion of the flexible braided tube (20) with a polymer coating. In another embodiment, the braid filaments may be prevented from moving relative to each other by exposure of such portion of the flexible braided tube (20) to a temperature equivalent to or higher than the melting point of the braid filaments which may be done by exposure of the braid filaments at their intersection points to a heating element such as a soldering iron.

The selectively lockable braided flexible tube (20) may be used to perform various minimally invasive surgical procedures. The method may involve the steps of inserting an endoscope (40) (including without limitation a standard endoscope) into a selectively lockable flexible braided tube, introducing the endoscope (40) and the flexible braided tube (20) assembly into a patient's natural orifice and guiding the assembly in a patient's alimentary tract lumen, the alimentary tract lumen being defined by the alimentary tract wall. The method may further involve the steps of perforating the alimentary tract wall into the patient's abdominal cavity; locating a target site in the abdominal cavity for a the surgical procedure, positioning the assembly relative the target site, locking the flexible braided tube into desired configuration, and performing such surgical procedure through the perforation.

Figure 6:
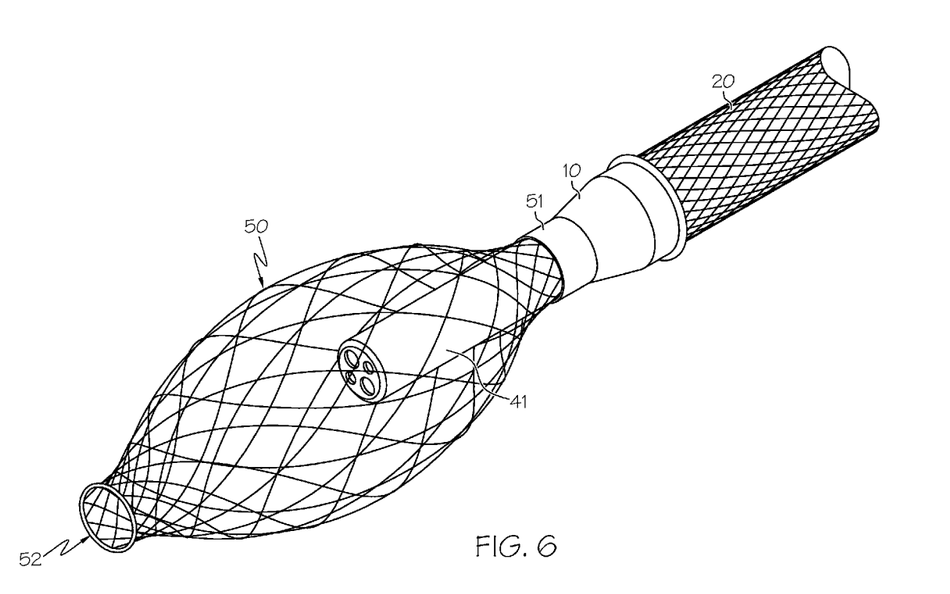
FIG. 6 depicts a braided basket.
Figure 7:
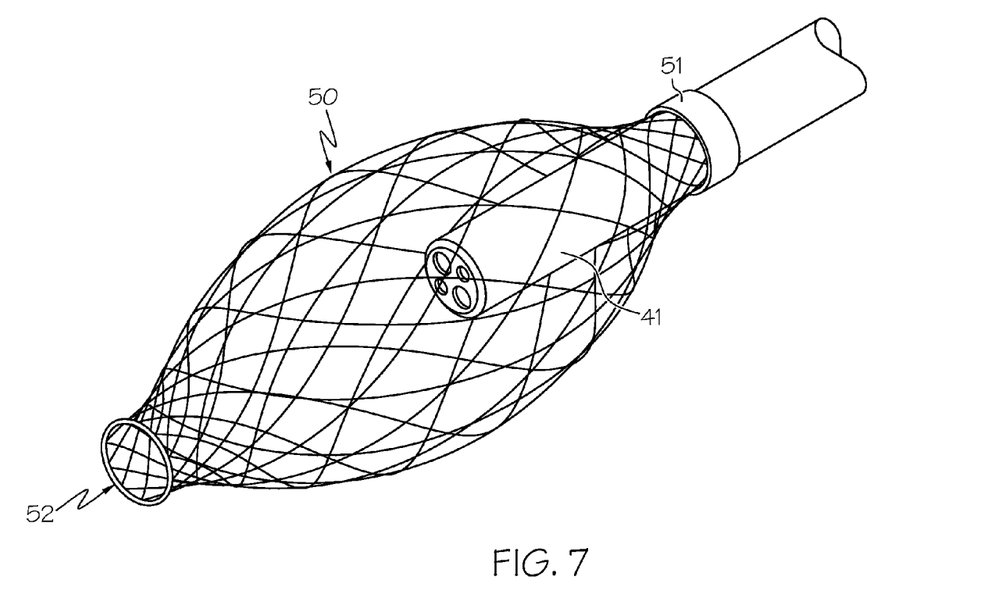
FIG. 7 depicts a braided basket.

FIG. 6 comprises a braided hollow member (50) attached to the distal end of the braided device. In one embodiment, the distal portion of the braided flexible tube (20) can be formed into the braided hollow member (50). In another embodiment, the braided hollow member (50) may have a proximal collar (51) that can be molded or attachable to the distal end of the braided device such that the collar may receive and allow the passage of a distal portion of a standard endoscope (41). The braided hollow member (50) may provide the space for the distal portion of a standard endoscope (41) to articulate freely specially while performing a procedure in a patient's body cavity. The braided hollow member (50) may also comprise a distal opening (52) to allow the standard endoscope (40) to manipulate tissue through it. The standard endoscope (40) may also manipulate tissue through the windows of the braided hollow member (50). The braid filaments of the braided hollow member (50) may be comprised from, a variety of different materials such as for example polyamide, polyalkane, polyurethane, PET, PBT, Nylon, PEEK, PE, Glass Fibre, Metal Wire or Acrylic materials or any composition of the mentioned materials. The braided hollow member (50) may also be used as an independent device separate from the braided device as shown in FIG. 7. In this embodiment, the braided hollow member (50) may comprise a collar (51) at its proximal end. The collar (51) may be attached to a distal portion of a standard endoscope (41) prior to insertion of the standard endoscope (40) into a patient's body.

Figure 8:
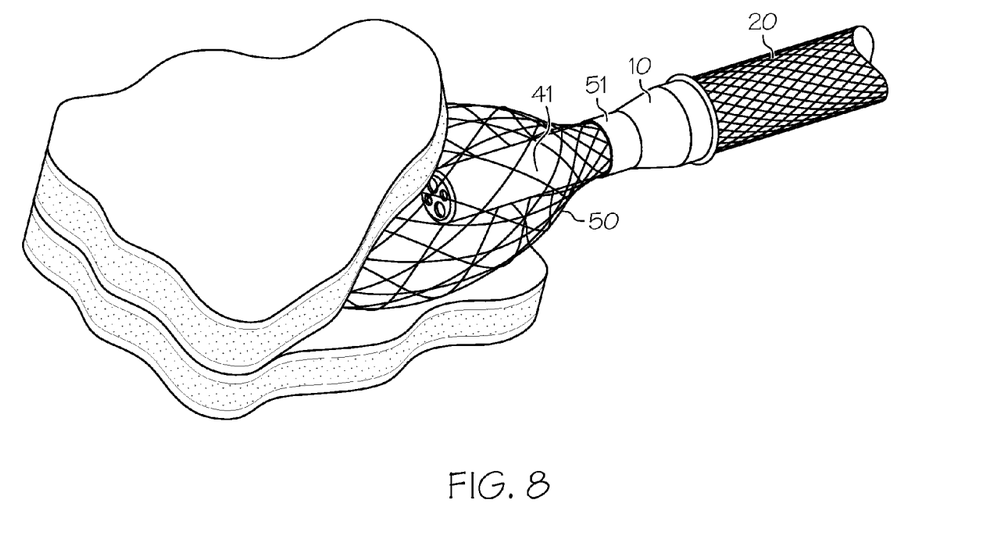
FIG. 8 depicts a braided basket with tissue.

FIG. 8 depicts the braided hollow member (50) in use with a standard endoscope (40) in lifting tissue and allowing the standard endoscope to reach interior layers. This provides a clear advantage for performing certain surgical procedures where the standard endoscope (40) needs to reach between tissue layers to operate on a desired target site. For example, in removing a gall bladder, a surgeon generally needs to raise a liver lobe in order to expose the gall bladder prior to its removal. The flexible nature of a standard endoscope (40) becomes a disadvantage in performing such a surgical procedure. The braided device may provide the selective stiffness and overall stability that the standard endoscope (40) needs to perform such surgical procedure once it reaches the target site and the braided hollow member (50) may provide the space needed for working between tissue layers.

Figure 9:
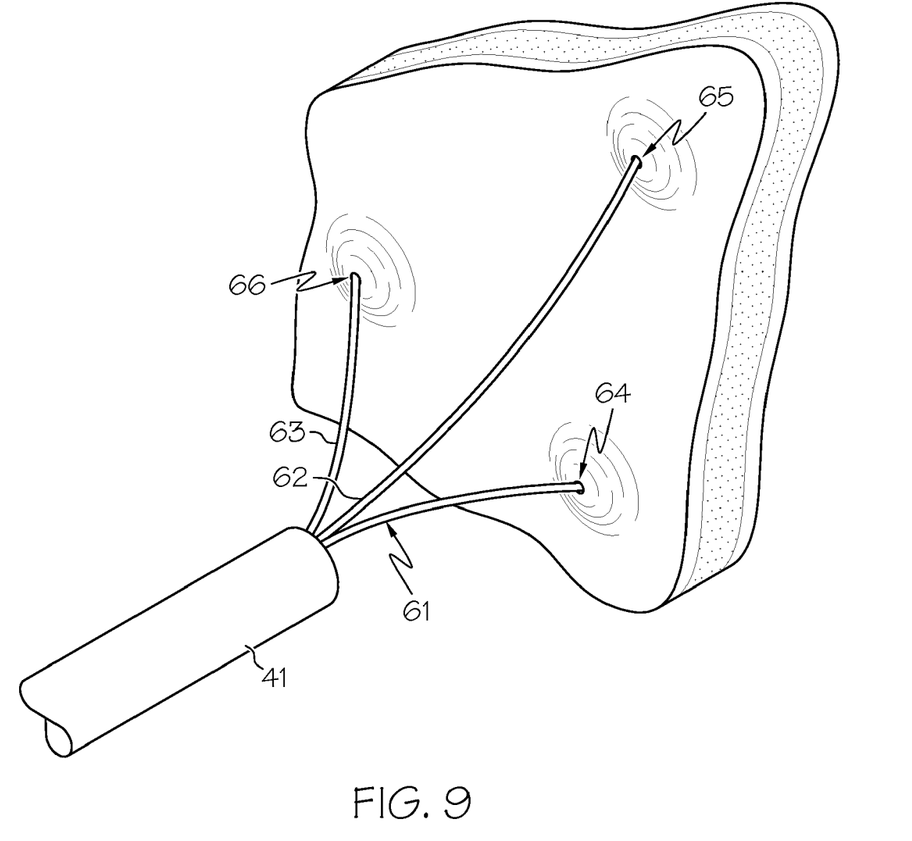
FIG. 9 depicts an endoscopic device with sutures anchored into tissue.

FIG. 9 depicts a method of the current invention for stabilizing a standard endoscope (40) and maintaining its view during a surgical procedure. As discussed above, the flexible nature of a standard endoscope (40) may become a disadvantage when manipulating tissue specially while using an endoscope's accessory such as a pair of graspers to retract tissue. Once the standard endoscope (40) reaches the target site and the graspers are extended to grab the tissue to be retracted, the standard endoscope (40) being essentially a flexible tube, sometimes changes position as a response to the retraction force which leads to a loss of the operator's view of the target site. The operator has to re-find the target site and start over again. The method shown in FIG. 8 suggests anchoring one or more sutures at the target site, which are extended through a standard endoscope's accessory, channel towards a proximal opening of the accessory channel and are controlled by the operator. The sutures may allow the standard endoscope (40) to return to the exact target site of the surgical procedure. One advantage of using sutures is due to the fact that they are readily available in an operating room and that they are small in diameter, which means that the accessory channel will remain available for use with other accessories that the operator may decide to apply. People with ordinary skill in the art will appreciate that the use of sutures in this method is only one example and other variations are possible. For instance, wires or cables or elastic bands may be used instead. The sutures may be directly sutured at the target site or anchored using a variety of different ways. T-tags, hooks, or clips may be attached to the distal ends of sutures and anchored at the target site. In a preferred embodiment, three sutures (61 & 62 & 63) are anchored at three different locations (64 & 65 & 66) at the target site, which may stabilize the standard endoscope (40) in view of the target site and may also play a role in accurate presentation and manipulation of the target site for utilization of various endoscopic accessories. For example, the operator may turn the tissue into a desired angle by slightly releasing one of the sutures and slightly retracting the other two sutures instead of having to adjust the standard endoscope (40) to the angle needed to perform its function.

Figure 10:
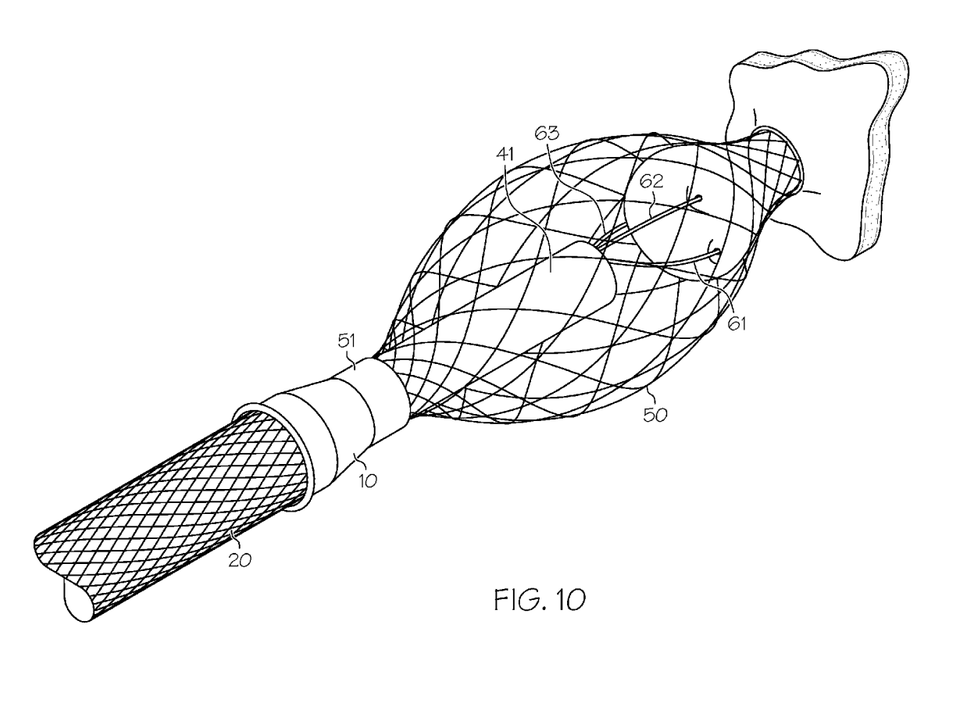
FIG. 10 depicts a braided basket with tissue.

FIG. 10 depicts a step of a surgical method of the current invention for removal of tissue from an internal body cavity such as the peritoneal cavity via a standard endoscope (40). In this embodiment, a standard endoscope (40) may be utilized in combination with the braided device and braided hollow member (50) assembly. The standard endoscope (40) may be inserted into the central lumen (5) of the braided device. They may then be advanced into a patient's natural orifice and guided through an internal body lumen where the standard endoscope (40) may be used to perforate a wall of the body lumen into a patient's internal cavity. At this point, the braided device may be utilized to further steer and hold the standard endoscope (40) in a position facing a target site. If the target site is hidden such as for example by another organ, the braided hollow member (50) may then be utilized to create the space needed for the standard endoscope (40) to perform its function. Once the target site is reached, sutures may be anchored to the tissue to be removed as described above and the operator may then utilize the sutures to adjust and manipulate the tissue for excision. The excised tissue may then be retracted into the braided hollow member (50) by pulling on the sutures.

Preferably, the devices described above will be processed before surgery. First, a new or used braided device is obtained and if necessary cleaned. The braided device can then be sterilized. In one sterilization technique, the braided device is placed in a closed and sealed container, such as a plastic or TYVEK bag. Optionally, the braided device can be bundled in the container as a kit with other components. The container and braided device, as well as any other components, are then placed in a field of radiation that can penetrate the container, such as gamma radiation, x-rays, or high-energy electrons. The radiation kills bacteria on the braided device and in the container. The sterilized braided device can then be stored in the sterile container. The sealed container keeps the braided device sterile until it is opened in the medical facility.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. As a further example, many embodiments were discussed in the context standard endoscopes, but the teachings herein are also applicable with other endoscopes. Accordingly, the scope of the present invention should be considered in terms of the following claims and is understood not to be limited to the details of structure, materials, or acts shown and described in the specification and drawings.

The invention claimed is:

1. A surgical method, comprising:
   a) introducing an endoscope into a patient's natural orifice;
   b) guiding the endoscope in a patient's alimentary tract lumen, the alimentary tract lumen being defined by the alimentary tract wall;
   c) anchoring one or more sutures at a target site for the surgical procedure;
   d) tensioning the sutures to position the endoscope and to maintain the target site within a field of view of the endoscope while the sutures pass through a channel of the endoscope; and
   (e) performing a surgical endoscopic procedure from the repositioned endoscope.

2. The method of claim 1, wherein the sutures pass through the endoscope working channel.

3. The method of claim 1, wherein step (c) comprises anchoring a plurality of sutures.

4. The method of claim 3, wherein the plurality of sutures pass through the accessory channel of the endoscope.

5. The method of claim 4, further comprising:
selectively releasing and retracting the plurality of sutures to present and manipulate the target site.

6. The method of claim 1, wherein step (c) comprises anchoring three sutures at three different locations.

7. The method of claim 6, wherein the three different locations define a triangle.

8. The method of claim 7, further comprising selectively releasing and retracting the plurality of sutures to present and manipulate the target site.

9. The method of claim 8, wherein the three sutures pass through an accessory channel of the endoscope.

* * * * *